United States Patent [19]

Fite

[11] 4,209,696
[45] Jun. 24, 1980

[54] METHODS AND APPARATUS FOR MASS SPECTROMETRIC ANALYSIS OF CONSTITUENTS IN LIQUIDS

[76] Inventor: Wade L. Fite, 305 Pasadena Dr., Pittsburgh, Pa. 15215

[21] Appl. No.: 14,948

[22] Filed: Feb. 26, 1979

Related U.S. Application Data

[63] Continuation of Ser. No. 835,160, Sep. 21, 1977, abandoned.

[51] Int. Cl.$^2$ ............................................... B01D 59/44
[52] U.S. Cl. .................................... 250/281; 250/288
[58] Field of Search ................................ 250/281, 288

[56] References Cited

U.S. PATENT DOCUMENTS

| | | | |
|---|---|---|---|
| 4,023,398 | 5/1977 | French et al. | 250/281 |
| 4,121,099 | 10/1978 | French et al. | 250/281 |
| 4,144,451 | 3/1979 | Kambara | 250/281 |

OTHER PUBLICATIONS

"Electrohydrodynamic Ion Source", by Mahoney et al., Journal of Applied Physics, vol. 40, No. 13, Dec. 1969, pp. 5101-5106.

*Primary Examiner*—Harold A. Dixon
*Attorney, Agent, or Firm*—Mason, Mason and Albright

[57] ABSTRACT

Methods and apparatus for mass analysis of molecular constituents of liquids, including minor constituents, in which an electrospray technique produces electrically charged droplets which divide and evaporate to form gaseous ions of the molecular constituents. The ions are then drawn through suitable differential pumping and focusing arrangements into a mass-to-charge analyzer. A charged capillary tube extending into a small chamber couples a liquid chromatograph or other source of liquid with a mass spectrometer, the electrospray technique being applied in the small chamber as a result of a charged liquid discharged from the capillary tube.

42 Claims, 9 Drawing Figures

METHODS AND APPARATUS FOR MASS SPECTROMETRIC ANALYSIS OF CONSTITUENTS IN LIQUIDS

This is a continuing application of application Ser. No. 835,160, filed Sept. 21, 1977, now abandoned.

BACKGROUND OF THE INVENTION

The invention relates to a method and apparatus for spectrometric analysis of liquids such as may be received from a liquid chromatograph.

In the mass spectral analysis of molecular constituents dissolved or suspended in liquids, a frequently used technique is to place a sample of the liquid on a surface and allow the liquid to evaporate, leaving a solid residue of the molecular components from the liquid. Thereafter this residue is heated to drive the molecules into the vapor phase, after which the molecules are ionized by electron impact. The ions are then analyzed for their mass-to-charge ratio using ion separation in magnetic fields, time varying quadrupole electrical fields or other ion mass spectrometer techniques.

This approach is satisfactory if the molecule is sufficiently volatile to enter the vapor phase prior to undergoing thermal decomposition.

For those molecules which thermally decompose before evaporating, another technique is to place a drop of liquid on an array of very fine needle points or sharp edges of an electrically conducting material and then apply a high voltage to the material. The very strong electric fields in the immediate vicinity of the points or edges assist the molecules in leaving the surface and furthermore when a molecule leaves it is as an ion, i.e. an electrically charged molecule. These techniques, which are often used in conjunction with heating, are called Field Ionization and Field Desorption Ionization.

The present invention utilizes another method to produce gaseous ions, of both volatile and nonvolatile molecular constituents of liquids, which incorporates a technique called "electrospray." Although it applies generally to liquids which can evaporate, it is of particular interest when used to couple mass spectrometers to liquid chromatographs.

Gas chromatographs and liquid chromatographs are used to separate mixtures of molecules which are then detected in an appropriate manner. A commonly used instrument at present is the gas chromatograph-mass spectrometer (GC/MS) combination where the detector is a mass spectrometer.

Gas chromatographs require that the molecules be volatile so that they can be suspended in the carrier gas used in the gas chromatograph and high temperatures of up to several hundred degrees Celsius are required in some cases to volatilize the molecules in the sample detected. Although this is satisfactory for many molecules, many other molecules of interest to the analytical chemist or biologist tend to decompose at high temperatures before they are volatilized.

The liquid chromatograph is similar to a gas chromatograph except that a liquid is used as the carrier substance rather than a gas. In the liquid chromatograph the sample molecules are suspended in a liquid at low temperature, so that there is no tendency for the molecule to decompose thermally. The problem with coupling a liquid chromatograph, which separates the molecules in a mixture, with a mass spectrometer which uniquely identifies each of the molecule components in the mixture is first of getting the molecules into the vapor phase and next electrically charging the molecules, either positively or negatively, to form ions which can then be separated in the charge-to-mass analyzer of the mass spectrometer.

A method of accomplishing the task of simultaneous volatilizing and charging molecules which makes use of electrospray techniques is described by Malcolm Dole and his associates (Journal of Chemical Physics, Volume 49, page 2240 (1968) and Volume 52, page 4977 (1970). In the technique, a liquid is passed through a capillary tube made of metal on which a high voltage is placed. As the liquid emerges from the capillary, it is subjected to a very strong electric field in the vicinity of the end of the capillary. The strong field polarizes the liquid at the end of the capillary, causing an elongated liquid filament to be formed and then normal surface tension forces produce instabilities which snap off a length of the filament to form a small droplet. Inasmuch as the snapping off of the filament occurs while the filament is in the strong electric field, the droplet formed is highly charged electrically. The electric fields acting on the charged droplet tend to accelerate the droplet away from the end of the capillary.

If the liquid is volatile it tends to evaporate and the droplet diminishes in size. If no charge leaks off the droplet while it is evaporating, the charge density on the surface of the droplet increases. When the surface charge density is low, the surface tension forces which tend to hold the droplet together in a spherical shape exceed the electrical repulsive forces caused by the surface charge density, and the droplet retains a spherical shape. However, as the droplet evaporates without loss of charge, there is a point reached where the electrical repulsive forces exceed the attractive surface tension forces whereupon the droplet becomes unstable and tends to break up into two or more smaller charged droplets. This point is called the Rayleigh instability limit and is characterized by the formula $$n = (2\pi TD^3)^{\frac{1}{2}}/e$$

where n is the total number of electronic charges on the droplet, e is the electronic unit of charge ($1.6 \times 10^{-19}$ coulombs), T is the surface tension and D is the diameter of the droplet. (Lord Rayleigh, Philosophical Magazine, Vol. 14, page 184 (1882)).

It has occurred to the inventor that these effects may be advantageously utilized for the purpose of producing gaseous ions of constituents of liquids including ions of molecules suspended or dissolved in a carrier liquid of liquid chromatographs. The molecular ions so produced then may be analyzed on the basis of their mass-to-charge ratio.

SUMMARY OF THE INVENTION

In the instant invention, a carrier liquid containing molecules to be analyzed, which includes molecules of a sample to be analyzed in the case of the liquid being the carrier liquid of a liquid chromatograph, is caused to flow under external pressure through a capillary tube of small bore. The capillary tube is composed of metal or other conducting material and is placed at a high electric potential ranging from a few hundred volts to several ten thousands of volts. The end of the capillary tube protrudes into a small chamber, the interior of which is placed at a low potential in the range of a few volts to several hundred volts. The strong electric field between the end of the capillary tube and the interior of the small chamber causes the liquid to emerge from the capillary tube in the form of small droplets, with diameters on the order of 1 micron ($10^{-4}$ cm), which are highly charged electrically, having from a few hundred to many thousands of electronic charges on them.

The pressure of gas in the small chamber is maintained sufficiently high substantially to prevent the charged droplets, which are otherwise accelerated by the electric fields therein, from reaching its wall and also is maintained sufficiently high to hold the droplet in a state of suspension for a fraction of a second or longer. While being slowed and then suspended in the gas, the charged droplets evaporate some of their carrier liquid, divide into smaller droplets as the Rayleigh instability limit is reached and then continue to evaporate and divide until finally the droplet is completely evaporated leaving neutral molecules of the carrier liquid, now in the vapor phase, and charged gaseous molecular ions of the constituents of the liquid. In practice much, if not all, gas contained in the small chamber is the vapor of the carrier liquid, however, optionally, other gas is admitted to maintain the pressure therein at the desired level.

The small chamber is provided with an aperture through which gas enters a second chamber which is maintained at a high vacuum. The gas in the small chamber, now containing gaseous molecular ions of the constituents of the liquid, moves under the hydrodynamic flow towards and through the aperture, a free jet expansion occurring in the vacuum of a second chamber. Electrodes placed just inside the second chamber and near the aperture, accelerate the ions, separate them from the neutral molecules in the free jet expansion and focus them into a mass-to-charge analyzer (ion mass spectrometer) for analysis.

The ion energy of the ions for analysis is determined by the value of the low potential placed on the interior walls of the initial small chamber. When this potential is positive the positive ion mass spectrum is obtained, and when it is negative, the negative ion mass spectrum is obtained.

High accelerating electric fields can be placed immediately after the ions enter the second chamber to cause the molecular ions to be fragmented by collisions with neutral molecules in the free jet expansion. Such fragmentation is desired in many cases to aid in the positive identification of the constituents of the liquid.

An electron gun provided in the second chamber permits electron-impact ionization of the neutral molecules in the free jet expansion.

More than one chamber operating at high vacuum may be employed for the purpose of using multiple differential pumping.

DESCRIPTION OF THE INVENTION

An important aspect of the invention involves the use of electrospray techniques to produce, in a single operation, gaseous ions of molecules of both major and minor constituents in the liquid. The method is particularly attractive because gaseous ions of nonvolatile as well as volatile constituents of the liquid are formed and it is especially attractive for application to the mass analysis of the effluents of liquid chromatographs.

The formation of highly charged droplets with diameters of the order of $10^{-4}$ cm and total charge of the order of $1.5 \times 10^{-15}$ coulombs ($10^4$ electronic charges) is accomplished by placing an electric potential ranging from a few hundred volts to several tens of thousands of volts on a metallic capillary tube, the tip of which is located a small distance (ranging from a few millimeters to several centimeters) away from another conducting surface at a potential near or at ground potential. The strong fields present at the sharp tip of the capillary tube cause the liquid as it emerges from the tube to form into a filament, a section of which then snaps off under the instabilities created by the surface tension forces of the liquid. The surface tension forces then cause the liquid of the snapped off section of the filament to assume a spherical shape, the sphere being highly electrically charged.

The strong electric fields in the immediate vicinity of the tip of the capillary accelerate the charged droplet away from the tip of the capillary tube. This acceleration diminishes rapidly as the droplet moves away from the tip of the capillary tube where the electric fields become weaker.

The capillary tube extends inside a small chamber, the interior surface of which is held at a low potential as indicated above. The electric field inside such small chamber is produced by the difference of potentials applied to the capillary tube and the interior walls of the small chamber.

The gas pressure inside the small chamber is selected primarily on the basis of two considerations. The first is that it should be sufficiently high that the motion of the charged droplet is retarded and effectively stopped in the gas of the small chamber before it reaches a wall. The retardation of the droplet is controlled by viscous forces of the gas in the small chamber operating on the droplet which is moving with respect to the gas in the small chamber. The Stokes formula gives this force for the droplet when it is still larger than about one micron and the force is equal to $F = 6\pi \eta a v$, where $\eta$ is the coefficient of viscosity, a is the radius of the droplet and v is the relative velocity of the droplet with respect to the gas. Since the coefficient of viscosity increases with increasing gas pressure, a minimum pressure may be prescribed for a given gas and a given distance from the tip of the capillary tube to the interior walls of the small chamber. In practice, it is found that a pressure which is near atmospheric pressure gives a stopping distance for electrosprayed droplets of the order of one centimeter. Other pressures ranging from about 100 torr to 10 atmospheres in the small chamber provide a range of different stopping distances whereby the small chamber may be either larger or smaller.

A second important consideration is to exclude laboratory air from entering the small chamber so that the ions formed in the small chamber are limited to those representative of the liquid being analyzed. This recommends that the pressure in the chamber be greater than atmospheric pressure in which case the small chamber need not be completely airtight.

The pressure in the small chamber can frequently be entirely produced by the vapor from the evaporating droplets. However, in some cases it is desirable to supplement the gas pressure by introducing additional clean gas.

The droplets, once effectively stopped in the gas in the small chamber, are subjected to relatively small electric fields far removed from the sharp tip of the capillary tube and also to gravity force. These forces plus the Stokes viscous force determine the motion of the droplet which, at near atmospheric pressure, is very slow thus allowing the droplet to be suspended almost motionlessly with respect to the gas.

The carrier liquid, which makes up the bulk of the material in the droplet, evaporates in the gas in the small chamber. To assist this evaporation, it is desirable to heat the small chamber so that thermal energy needed for evaporation of the carrier liquid can be brought to the droplet by conduction and convection in the gas in the small chamber.

As the droplets evaporate they are reduced in size until the Rayleigh instability limit is reached at which time the repulsive forces from the electric charge on the droplet cause it to divide into two or more smaller droplets, which then continue to evaporate until the next Rayleigh instability limit is reached when division again takes place, followed by more evaporation and division, until finally the droplet is completely evaporated leaving only neutral molecules and molecular ions of the constituents of the liquid in the gas inside the small chamber. The ions formed are generally those which have been formed under the action of ion-molecule reactions between the ions of the carrier liquid and the molecules of constituents other than the carrier liquid. The ions are thus similar to those that are seen in a so-called "chemical ionization" spectrum where the primary ions are those of the carrier liquid vapor.

For mass-to-charge analysis of the ions now in the gas inside the small chamber, the gas must be conducted to a mass-to-charge analyzer and this is accomplished by providing a small pinhole aperture in a wall of the small chamber through which the gas flows into a region of high vacuum. The gas in the small chamber, containing the ions to be analyzed, emerges from the small chamber and enters as a free jet expansion into the second chamber at the high vacuum. As the gas expands, it becomes less dense and the ions are no longer constrained to move with the gas, but can be affected by electric fields which accelerate the ions and focus them into the mass-to-charge analyzer. The mass-to-charge analyzer may, if desired, be located inside the second chamber operating at high vacuum. However, it has been found more satisfactory that the second chamber be an intermediate chamber, with a third chamber operating at a still higher vacuum housing the mass-to-charge analyzer.

The size of the pinhole aperture between the small chamber and the second chamber is determined by the pressure desired in the second chamber and by the speed of the pump evacuating the second chamber. Where the mass-to-charge analyzer is located in the second chamber, the pressure in the small chamber is preferably less than $10^{-4}$ torr. Assuming the pressure in the small chamber to be atmospheric pressure and the speed of the pump evacuating the second chamber to be 300 liters/second, known formulas on gas flow indicate that the area of the pinhole aperture sould be less than about $2 \times 10^{-6}$ cm$^2$. Where differential pumping is used and the pressure in the second chamber is made an order of magnitude higher, the area of the pinhole aperture is increased accordingly. This is desirable inasmuch as the aperture need not be cleaned as frequently as required otherwise.

As noted above, the ions that emerge from the small chamber through the pinhole aperture are those produced by chemical ionization between ions of the carrier liquid vapor and the other constituents in the liquid. Although these spectra are relatively simple, tending to include relatively few fragment ions of the other constituents, it is often desired to obtain mass spectra from constituent ions which have been highly fragmented. This is accomplished in the present invention by applying a very high accelerating field to the free jet expansion in the second chamber. Ions accelerated by this field gain sufficient energy that they are broken into fragments as they collide with the neutral molecules in the free jet expansion. Such fragment ions are then retarded after they are separated from the neutral molecules in the free jet expansion for focusing into the mass-to-charge analyzer.

By providing an electron gun in the second chamber neutral molecules in the free jet expansion are electron-impact ionized and the resulting ions are analyzed for mass-to-charge ratio.

The droplets are charged either positively or negatively, depending on the polarity of the high electrical potential placed on the capillary tube, and both positive and negative ion spectra are thus obtainable by employing conventional positive or negative ion mass spectrometric methods and apparatus.

Capillary tubes have been constructed of 26 gauge hypodermic needles and potentials of from 300- to 10,000 volts have been applied to these needles. A mass analysis of the resulting ions was made using the differentially pumped vacuum system commercially sold as part of an atmospheric pressure ionization mass spectrometer by Extranuclear Laboratories, Inc. It was found, in using either acetone or ethanol as carrier liquids, ions other than those of the carrier liquid were produced. It was also found that the resulting ion spectra more nearly resembled those produced by atmospheric pressure ionization rather than low pressure chemical ionization. The spectra contained more heavy cluster ions than is usually found in low pressure chemical ionization.

Whereas the mass-to-charge analyzer was a quadrupole mass filter, other types of ion mass analyzers including magnetic ion mass spectrometers, time-of-flight mass spectrometers, linear accelerator type mass spectrometers, may be utilized with suitable modifications apparent to persons skilled in the mass spectrometric art.

Other objects, adaptabilities and capabilities of the invention will be appreciated from the following description, reference being had to the accompanying drawings, in which:

DESCRIPTION OF THE PREFERRED EMBODIMENTS

Figure 1:
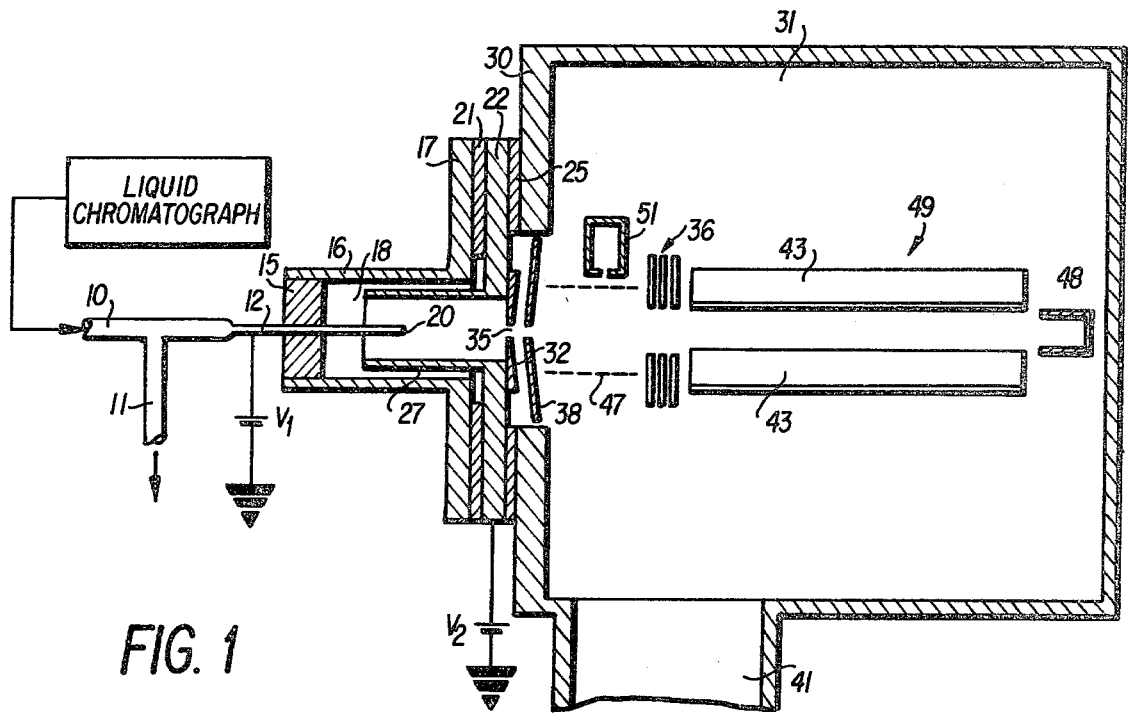
FIG. 1 is a sectional schematic depiction of the invention wherein a mass-to-charge analyzer is placed in a second chamber held at high vacuum.

Referring to FIG. 1, a preferred embodiment of the invention, liquid, which may be the carrier liquid from a liquid chromatograph, flows within a tube 10 and a portion of the liquid is caused to flow out of tube 11 which joins onto tube 10 as a Tee. A portion of the liquid also enters a fine-bore capillary tube 12 which enters into a small cylindrical chamber 18, enclosed and defined by walls 16 through a plug 15 composed of glass, lexan or other electrically insulating material which provides mechanical support for capillary tube 12. Capillary tube 12 is composed of electrically conducting material, usually a metal, and is electrically biased to a potential $V_1$ in the range from 100 volts to 30,000 volts. This potential is selectively either positive or negative depending on whether a positive ion or negative ion spectrum is desired for the molecules to be sampled. The tip of capillary tube 12 is open whereby liquid flows out of the tube and into the small chamber enclosed by walls 16. Walls 16 are connected to a metal flange 17 which mates to an insulating flange 21 which mates to metal flange 22, which, in turn, mates to a second insulating flange 25 which still further mates to an end wall 30 of the second chamber. Bolts which secure the sequence of flanges in place are not shown in the figure, these being well known to those skilled in vacuum techniques who will appreciate that such bolts must not make electrical contact with metal flange 22 and that many methods exist for ensuring this, among which is to position an insulating sleeve over the bolts at that place along their length coinciding with metal flange 22.

Attached to metal flange 22 is a reentrant hollow cylinder 27 which extends back into the small chamber towards plug 15 a sufficient distance so that the end of capillary tube 12 is received within hollow cylinder 27. An electrical potential $V_2$ of low voltage is placed on hollow cylinder 27 by a connection made at the outer periphery of metal flange 22. The electric field which forms the droplets in the electrospray process is that which exists between the end of capillary tube 12 and hollow cylinder 27 by virtue of the potential difference $(V_1-V_2)$ between these two elements. Potential $V_2$ determines the kinetic energy of the ions after they leave the small chamber via a pinhole aperture 35 and enter the high vacuum of a second chamber 31 which is maintained at a pressure less than $10^{-4}$ torr.

Attached to a metal flange 22 is a smaller flange 32 which has at its center pinhole aperture 35 connecting the small chamber in which the droplets are formed and the second chamber maintained at high vacuum. Flange 32 is removable from flange 22 for cleaning pinhole aperture 35. With an understanding of the invention, a number of detailed designs of smaller flange 32 will occur to those skilled in the art whereby pinhole aperture 35 constitutes the only opening between the small chamber in which the droplets are formed and the second chamber.

Immediately inside the second chamber at high vacuum, produced by a fast pump connected to a pumping port 41, is an element 38 to which electrical potentials are applied for accelerating the ions away from the pinhole aperture 35. Immediately after element 38 is an ion optical lens 47 of a cylindrical shape, the axis of said cylinder lens being coincident with the axis of the small chamber. Cylinder lens 47 is constructed of a high transparency metal mesh to permit non-ionized gas, which flows out of the pinhole aperture, to escape freely into the general volume of the second chamber from whence it is removed through pumping port 41. Immediately behind the mesh cylinder lens are one or more planar lenses 36 which are used to focus ions into the mass-to-charge analyzer 49 which is here shown to be a quadrupole mass filter, two poles 43 of which are shown in the drawing. At the opposite end of the quadrupole mass filter, or other mass-to-charge analyzer, is a detector 48 which is normally an electron multiplier but can be a Faraday cage or other conventional device for registering the arrival of ions.

Mounted outside mesh cylinder lens 47 is an electron gun 51 which can be a single thermionically emitting filament heated and biased at a negative potential so as, when desired, to cause thermionic electrons leaving the filament to be accelerated toward and through the mesh of cylinder lens 47 and thereafter create ions by electron impact within the mesh cylinder lens, said ions then being drawn toward and focused into the quadrupole mass filter. Those skilled in the art will recognize alternate means of providing an electron gun 51 and recognize that it can be mounted at various positions.

Although electrical isolation and biasing of hollow cylinder 27 is accomplished by the use of metallic flanges 17 and 22 and end wall 30 of the second chamber between which are flanges 21 and 25 of electrically insulating material, the use of other geometries which permit the use of bonded metal-to-ceramic or metal-to-glass seals can be substituted for the configuration shown in FIG. 1. Similarly, smaller flange 32, which contains the pinhole aperture 35 and is a single piece of machined metal, may be two metallic pieces which fit together whereby a metal foil containing the pinhole aperture is secured between the two metallic pieces in the manner currently used in atmospheric pressure ionization mass spectrometers of Extranuclear Laboratories, Inc. Other variations within the scope of the invention will occur to those skilled in the art.

When it is desired to fragment the molecular ions flowing from the small chamber, it is necessary only to increase the potential applied to lens element 38 whereby it is relatively very high (in the range of several hundred to several thousand volts). The accelerated ions then collide with the neutral molecules in the free jet expansion and break into fragment ions. As the fragment ions enter cylindrical lens 47 they are decelerated to an energy which permits their subsequent focusing into the mass-to-charge analyzer.

It will be readily apparent that there are alternative lens configurations which, although within the skill of the art, differ from those shown in the drawing, but are nevertheless satisfactory for the purpose of focussing the ions into the mass-to-charge analyzer. Such configurations may include more than one element composed of mesh.

Figure 2:
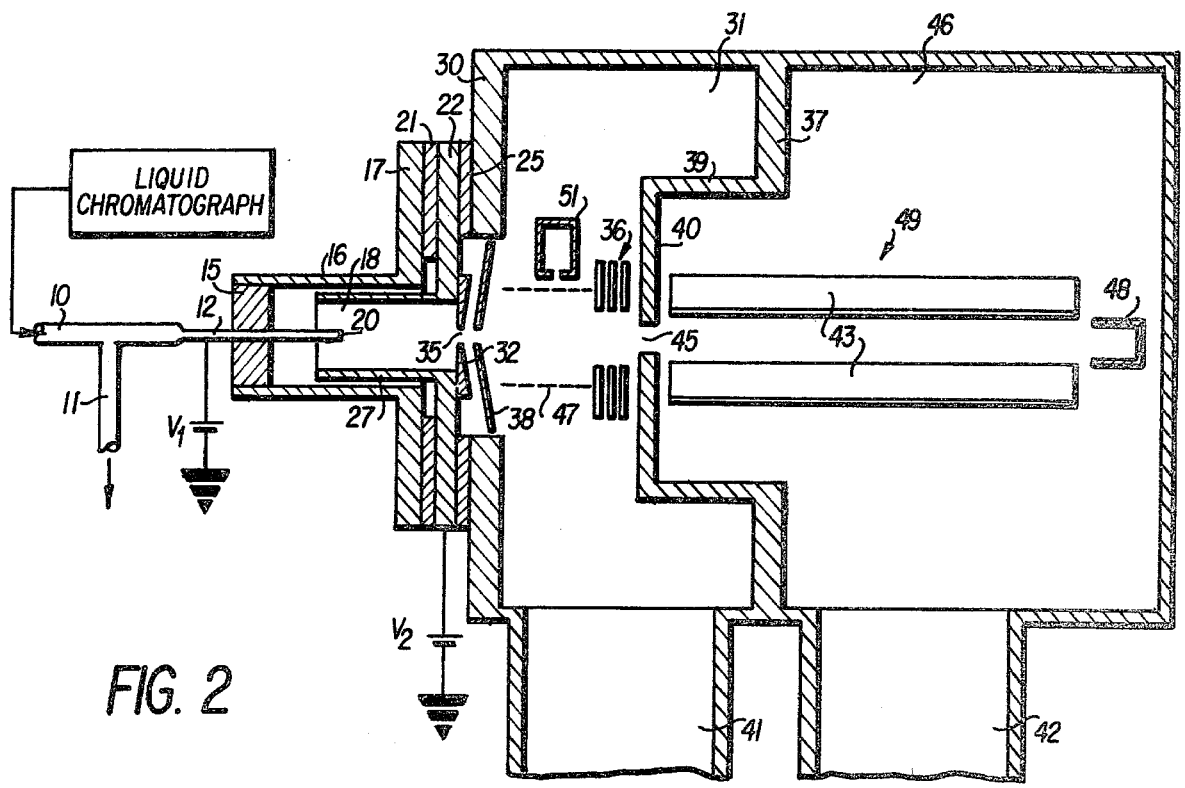
FIG. 2 is a sectional schematic representation of a further embodiment of the invention where differential pumping is used and where the second chamber contains lenses for accelerating and focusing the ions through an aperture and into a third chamber having a high vacuum in which the mass-to-charge analyzer is located.

FIG. 2 illustrates an embodiment of the invention where two chambers maintained at high vacuum are provided after small chamber 18. A suitable arrangement of the two chambers is shown in the figure wherein an annular wall 37 is located across the length of the main chamber 31 and a cylindrical tube 39 extends towards the small chamber, one end of said cylindrical tube 39 being welded or brazed to the inner diameter of annular wall 37. The other end of the cylindrical tube 39 is joined to a circular planar wall 40 which has a small aperture 45 having a diameter of two or three millimeters at its center. This design, using a reentrant cylinder, places the end of the mass filter 49 close to small chamber 18 which is the primary source of the ions and still leaves ample space and volume for a high speed pump such as a turbomolecular of other fast pump to be affixed to large pumping port 41. The mass-to-charge analyzer 49 and the ion detector 48 are mounted on the right of the separating wall (as seen in the figure) which is in a region of high vacuum, normally at a pressure of less than $10^{-5}$ torr, produced by a fast vacuum pump connected to a large pumping port 42 to evacuate the third chamber 46. The actual area of aperture 45 is determined by the speeds of the vacuum pumps used and the pressure desired in chamber 46, in which the mass-to-charge analyzer is located, and is readily determined from well known formulas on gas flow.

In this differentially pumped version of the invention, the planar lenses 36 focus the ions into aperture 45, rather than directly into the mass-to-charge analyzer, from whence they proceed into mass-to-charge analyzer 49. In this embodiment, because the mass-to-charge analyzer is not in second chamber 31 where the jet free expansion from the small chamber occurs, the pressure in the second chamber may be increased to more than $10^{-4}$ torr and this greater absolute pressure permits the pinhole aperture 35 in the small chamber to be larger, which is a convenience from the point of view of reducing the susceptibility of the pinhole aperture 35 to plug up.

Otherwise, the apparatus of FIG. 2 operates similarly to that of FIG. 1.

Figure 3:
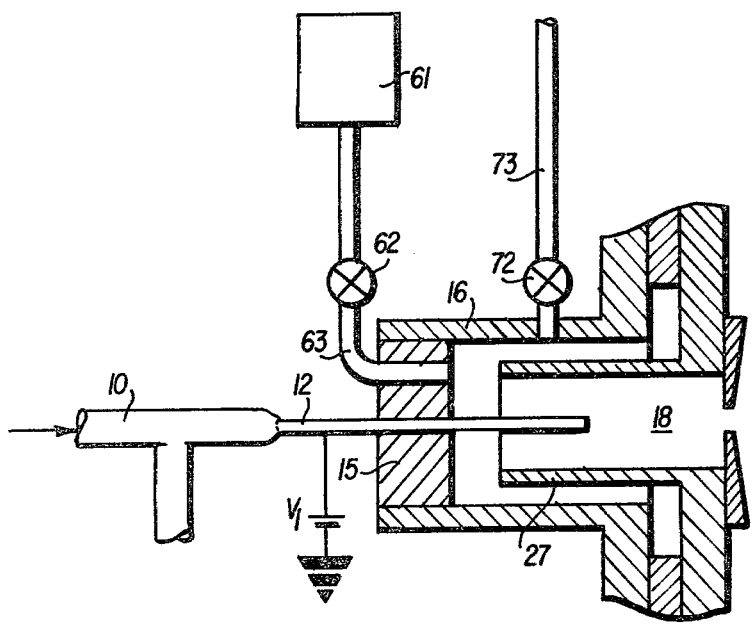
FIG. 3 is a detail sectional schematic illustration of the small chamber in which means to admit gas and remove gas therefrom are shown.

FIG. 3 shows two modifications to the small chamber, the first modification being one in which a gas such as nitrogen or argon or any other selected gas is additionally admitted to small chamber 18 to ensure that the pressure in the small chamber is near-atmospheric pressure or above atmospheric pressure as desired in the event that vaporization of the liquid droplets is insufficient to maintain the pressure desired. In this case the gas from a reservoir 61 passes through a controlled leak value 62 and thence via a tube 63 which is inserted through the insulating plug 15 into the small chamber. Tube 63, passing into small chamber 18 may optionally pass through metallic wall 16 instead of insulating plug 15.

FIG. 3 also shows a valve 72 which may be mounted directly on small chamber 18. This valve may optionally be a relief valve set to ensure that the pressure in the small chamber does not exceed a desired amount and, in this usage, a tube 73 vents directly into the atmosphere. When pressure in small chamber 18 is less than atmospheric pressure, tube 73 can be connected to a vacuum pump.

Figure 4:
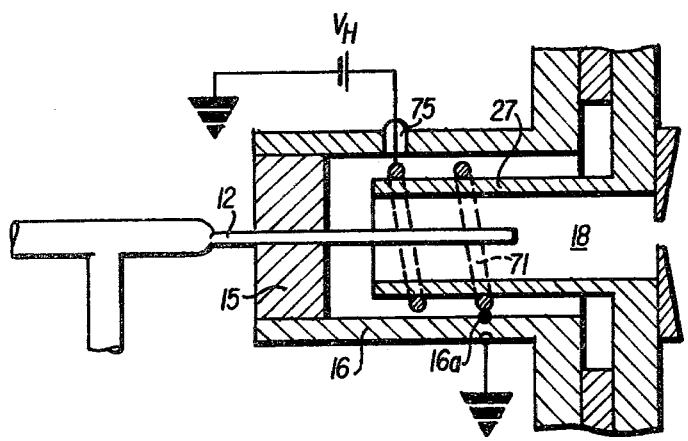
FIG. 4 shows a detail further sectional schematic illustration wherein means for heating the gas in the small chamber is shown.

FIG. 4 illustrates a further modification of small chamber 18 wherein a heater coil 71 which is mounted inside the small chamber between hollow metal cylinder 27 and outer wall 16 of the small chamber 18. Heater coil 71 provides additional heat, as required, to evaporate the droplets when the carrier liquid is not highly volatile. The electric current for the coil, which may be made of tungsten, platinum, tantalum, nichrome or any other standard heater wire material, is produced from a voltage source $V_H$ which connects to one end of heater coil 71 through a vacuum feedthrough 75. The other end of heater coil 71 is connected to metallic wall at a contact 16a of small chamber 18 which, in the interests of personnel safety, is normally at ground potential.

Other methods of providing heat to the gas in small chamber 18 may be employed including generally heating the entire small chamber from the outside by means of electrical heating tape, by infrared irradiation, or other conventional means.

It will be appreciated that the three modifications illustrated in FIGS. 3 and 4, and their variants, may be used either individually or in combination of any two, or in combination of all three.

Figure 5A:
FIGS. 5A–5E are five detailed sectional illustrations of alternate configurations for the end of the capillary tube.
Figure 5B:
Figure 5C:
Figure 5D:

FIGS. 5A through 5E are five details on various shapings of the end of the capillary tube 20. FIG. 5A shows the end ground off at a slant in the manner of hypodermic needles. This design results in a high electric field in the vicinity of the resulting sharp edge point 81 and accomplishes the electrospray of the carrier liquid using relativey low voltages $V_1$. FIG. 5B shows an end which has been ground so that cylindrical symmetry is maintained while retaining a sharp edge 82 for development of high fields while using relatively low voltage $V_1$. FIG. 5C illustrated an end of tube 20 wherein an alternate method of grinding same has been employed leaving a sharp annular edge 85 where high electric fields are developed using relatively low voltages $V_1$. The geometry of FIG. 5C is preferred where it is desired that the size of the electrosprayed droplets be small, whereas the geometry of FIG. 5B is preferred if slightly larger initial droplets are desired.

Figure 5E:

FIG. D shows a geometry where the annular end 86 is ground flat with the plane of grinding being prepencdicular to the axis of the capillary tube. This geometry is preferred for ease of manufacture, although to produce the high fields required for electrospray higher potentials $V_1$ are required. FIG. 5E shows a configuration where the capillary tube is cut off as in FIG. 5D but where thereafter the edge of the annular end 87 is rounded. This geometry is preferred where high voltages $V_1$ are intentionally desired or where it is desired to have a fairly strong electric field extending throughout the small chamber for purposes of minimizing the time that a droplet remains in the small chamber, i.e., in cases where the carrier liquid is highly volatile and where one wishes the chemical ionization processes in the small chamber to operate for as short a time as possible.

Electrical circuit for element 38, focusing components mesh 47 and lens 36 and electron sources 51 have not been specifically illustrated as being understood within the skill of the art.

Although the preferred embodiments of the invention are described herein, it is to be understood that the inventive concepts are capable of other adaptations and modifications within the scope of the appended claims which should therefore be construed to cover not only the corresponding structure, material or acts described in the specification but also equivalents thereof.

Having thus described my invention, what I claim as new and desire to secure by Letters of the United States is:

1. A method of obtaining a mass spectrometric analysis of the constituents of liquids wherein electrically charged droplets of the liquid are formed by an electrospray process, the method comprising the step of producing said droplets by causing the liquid to be analyzed to flow through a capillary tube of small bore which is placed at a high electrical potential whereby said droplets emerge from said tube in an electrically charged condition in a small chamber maintaining the pressure of the gas therein sufficiently high effectively to cause the droplets to become suspended in said gas for a sufficient period of time that said charged droplets completely evaporate leaving substantially only gaseous molecules and ions of the constituents of the liquid and ions formed by ion-molecule reactions, providing a pinhole aperture in said small chamber and causing gaseous molecules and ions in said small chamber to flow through said aperture into a second chamber by maintaining said second chamber at high vacuum, and the step of accelerating and separating said ions from the electrically neutral molecules and focusing said ions into a mass-to-charge analyzer.

2. A method in accordance with claim 1, wherein the liquid to be analyzed is the carrier liquid emerging from a liquid chromatograph and the constituents of the liquid include the samples which are separated by the operation of said liquid chromatograph.

3. A method in accordance with claim 1, wherein the electrospray process is accomplished by causing the liquid to flow through said capillary tube of small bore which is placed at a high positive electrical potential and thus positively charged droplets of said liquid are formed.

4. A method in accordance with claim 1, wherein the electrospray process is accomplished by causing the liquid to flow through said capillary tube of small bore which is placed at a high negative electrical potential and thus negatively charged droplets of said liquid are formed.

5. A method in accordance with claim 1, wherein only a portion of the available liquid to be analyzed is operated on by the electrospray process, the remaining portion of the liquid being diverted.

6. A method in accordance with claim 1, where the gas in said small chamber consists entirely of the vapor of the liquid to be analyzed.

7. A method in accordance with claim 1, where the gas in the small chamber consists of the vapor of the liquid to be analyzed and of additional gas admitted to the small chamber.

8. A method in accordance with claim 1, where gas in said small chamber is removed only by its passage through said pinhole aperture which is mounted in a separating wall between said small chamber and said second chamber maintained at high vacuum.

9. A method in accordance with claim 1, where gas in said small chamber is removed by its passage through said pinhole aperture which is mounted in a separating wall between said small chamber and said second chamber maintained at high vacuum and providing a separate flow passage leading through a pressure relief valve to ambient air.

10. A method in accordance with claim 1, where gas in said small chamber is removed by its passage through said pinhole aperture which is mounted in a separating wall between the small chamber and said second chamber maintained at high vacuum and by providing a separate flow passage leading to a pump withdrawing gas from said small chamber.

11. A method in accordance with claim 1, the gas pressure in said small chamber being maintained at a pressure between 100 torr and 10 atmospheres.

12. A method in accordance with claim 1, the gas in said small chamber being maintained at substantially atmospheric pressure.

13. A method in accordance with claim 1, the gas in said small chamber being heated thereby facilitating rapid evaporation of charged droplets therein.

14. A method in accordance with claim 1, wherein the interior walls of said small chamber are at a low potential thereby establishing the energy of said ions when they are received by said mass-to-charge analyzer.

15. A method in accordance with claim 1, wherein said mass-to-charge analyzer is a quadrupole mass filter.

16. A method in accordance with claim 1, wherein said mass-to-charge analyzer is a quadrupole mass filter which is mounted inside the second chamber which is maintained at high vacuum.

17. A method in accordance with claim 1, wherein said mass-to-charge analyzer is a magnetic ion mass spectrometer.

18. A method in accordance with claim 1, wherein a system of lenses are provided in said second chamber which accelerates the ions and focuses them into said mass-to-charge analyzer.

19. A method in accordance with claim 18, wherein at least one of said lenses comprises a transparent mesh and permits neutral molecules flowing from said small chamber to escape into the volume of said second chamber.

20. A method in accordance with claim 18, wherein at least one of said lenses is maintained at a high potential and causes the ions to be accelerated sufficiently to break them into fragment ions as they collide with neutral molecules in the same flow from said small chamber, said fragment ions being decelerated before entering said mass-to-charge analyzer.

21. A method in accordance with claim 1, wherein said mass-to-charge analyzer is mounted in a third chamber maintained at higher vacuum than said second chamber into which the gas flows from said small chamber.

22. A method in accordance with claim 21, wherein lenses are provided to focus the ions into an aperture provided in the wall separating the second and third chambers.

23. Apparatus for the mass analysis of molecular constituents of liquids which comprises a first chamber, means comprising a capillary tube of small bore maintained at a relatively high electrical potential for introducing a liquid including the constituents to be analyzed into said first chamber, electrospray means comprising the outlet of said capillary tube in said first chamber for forming electrically charged droplets of said liquid, means for holding a gas at sufficient pressure in said first chamber for retaining said droplets therein for a sufficient period of time until they are completely evaporated leaving substantially only gaseous molecule ions of the constituents of the liquid droplets and ions formed by ion-molecule reactions, a second chamber adjacent said first chamber, a pinhole aperture between said first chamber and said second chamber, vacuum producing means connected to said second chamber for maintaining a substantially high vacuum therein, focusing means in said second chamber for accelerating and separating ions received through said pinhole from said first chamber and for focusing said ions into the entrance of a mass-to-charge analyzer.

24. Apparatus in accordance with claim 23, in combination with an outlet of a liquid chromatograph, the liquid introduced into said first chamber including samples which are separated by operation of said liquid chromatograph.

25. Apparatus in accordance with claim 23, wherein a wall is provided between said first chamber and said second chamber, said pinhole aperture being provided in said wall, at least part of said focusing means being mounted on said wall.

26. Apparatus in accordance with claim 23, wherein said capillary tube receives only a portion of the available liquid to be analyzed, means being provided for diverting the remaining portion of said liquid.

27. Apparatus in accordance with claim 23, wherein said gas contained in said first chamber consists entirely of the vapor of the liquid to be analyzed.

28. Apparatus in accordance with claim 23, wherein means for admitting gas other than vapor of the liquid to be analyzed is connected to said first chamber.

29. Apparatus in accordance with claim 23, wherein a separating wall is provided between said first chamber and said second chamber, said pinhole aperture being mounted on said separating wall.

30. Apparatus in accordance with claim 23, wherein a pressure relief valve is provided on said first chamber, said pressure relief valve leading to the atmosphere.

31. Apparatus in accordance with claim 23, wherein a pressure relief valve is provided on said first chamber, said pressure relief valve being connected to a vacuum source for withdrawing gas from said first chamber and maintaining same at a predetermined absolute pressure.

32. Apparatus in accordance with claim 23, wherein a pressure relief valve is provided on said first chamber, said pressure relief valve maintaining the pressure in said first chamber between 100 torr and 10 atmospheres.

33. Apparatus in accordance with claim 23, wherein said gas contained in said first chamber is at substantialy atmospheric pressure.

34. Apparatus in accordance with claim 23, wherein heating means is provided for said first chamber whereby rapid evaporation of the charged droplets in said first chamber is facilitated.

35. Apparatus in accordance with claim 23, wherein means for maintaining the interior wall defining said first chamber at a low electrical potential whereby the energy of said ions when they are received by said mass-to-charge analyzer is established by the low potential of said first chamber.

36. Apparatus in accordance with claim 23, in combination with a mass-to-charge analyzer which receives ions focused by said focusing means, said mass-to-charge analyzer being a quadrupole mass filter.

37. Apparatus in accordance with claim 36, wherein a third chamber is provided adjacent said second chamber with a further aperture provided between said second chamber and said third chamber, said quadrupole mass filter being arranged in said third chamber, means for maintaining a vacuum in said third chamber higher than the vacuum being maintained in said second chamber.

38. Apparatus in accordance with claim 23, in combination with a mass-to-charge analyzer which receives ions focused by said focusing means, said analyzer being a magnetic ion mass spectrometer.

39. Apparatus in accordance with claim 23, wherein said focusing means includes a system of lenses, at least one of said lenses comprising a transparent mesh which permits neutral molecules flowing from said first chamber to said second chamber to be separated from said ions flowing from said first chamber to said second chamber.

40. Apparatus in accordance with claim 39, wherein means for maintaining at least one of said lenses at a high electrical potential is provided, said potential being sufficiently high that it causes ions influenced by said lenses to be accelerated sufficiently to break them into fragment ions as they collide with neutral molecules in the same flow from said small chamber, further means being provided in said focusing means for decelerating said fragment ions before they are received by said mass-to-charge analyzer.

41. Apparatus in accordance with claim 23, in combination with a mass-to-charge analyzer, said mass-to-charge analyzer being received in said second chamber.

42. Apparatus in accordance with claim 23, wherein an electron gun is provided in said second chamber for selectively electron-impact ionizing neutral molecules emerging from said first said chamber.

* * * * *